United States Patent [19]
Lee et al.

[11] Patent Number: 5,569,447
[45] Date of Patent: Oct. 29, 1996

[54] STANNYLATED 3-QUINUCLIDINYL BENZILATES AND METHODS OF PREPARING RADIOHALOGENATED DERIVATIVES

[75] Inventors: Kan S. Lee, Rockville; Xiao-Shu He, Bethesda, both of Md.; Daniel R. Weinberger, Washington, D.C.

[73] Assignee: The United States of America represented by the Secretary Department of Health and Human Services, Washington, D.C.

[21] Appl. No.: 229,837

[22] Filed: Apr. 19, 1994

[51] Int. Cl.$^6$ .................. A61K 51/04; C07D 453/02; A01N 43/90
[52] U.S. Cl. .................. 424/1.85; 546/137; 514/305
[58] Field of Search .................. 424/1.61, 1.65, 424/1.85, 1.89; 514/305; 546/137, 133

[56] References Cited

U.S. PATENT DOCUMENTS 5,274,121  12/1993  Jacobson et al. .

OTHER PUBLICATIONS

Cohen, V. I. et al., *J. Pharmaceutical Sciences* 78: 833 (1989).
Eckelman, W. C. et al., *Science* 223: 291 (1984).
Eckelman, W. C. et al., *J. Nucl. Med.* 26: 637 (1985).
Gibson, R. E. et al., *J. Nucl. Med.* 30: 1079 (1989).
Gibson, R. E. et al., *J. Nucl. Med.* 25: 214 (1984).
Holman, B. L. et al., *JAMA* 254: 3063 (1985).
Kabalka, G. W. et al., *Nucl. Med. Biol* 16: 359 (1989).
Lee, K. S. et al., *J. Nucl. Med.* 27: 1045 (1986).
Neumeyer, J. L. et al., *J. Med. Chem.* 34: 3144 (1991).
Owens J., et al., *J. Labelled Compounds and Radiopharmaceuticals* 31: 45 (1991).
Palacios, J. M. et al., *Progress in Brain Research* 84: 243 (1990).
Rzeszotarski, W. J. et al., *J. Med Chem.* 27: 156 (1984).
Sawada, Y. et al., *Cereb. Blood Flow Metab.* 10: 781 (1990).
Weinberger, D. R. et al., *J. Neuropsychiatry & Clin. Neurosciences* 4: 239 (1992).
Sexton et al., *Soc. Neurosci. Abstr.* 17 (1–2) (1991).
Weinberger, D. R. et al., *Clin. Neuropharm* (Supp 1): 194A (1992).
Weinberger, D. R. et al., *Arch Neurol.* 48: 239–248 (1991).

*Primary Examiner*—Gary E. Hollinden
*Assistant Examiner*—Michael G. Hartley
*Attorney, Agent, or Firm*—Leydig, Voit & Mayer, Ltd

[57] ABSTRACT

The present invention provides stannylated 3-quinuclidinyl benzilate compounds and a method of synthesizing *AQNB by iodinating such stannylated 3-quinuclidinyl benzilate compounds. The iodination of these stannylated 3-quinuclidinyl benzilates proceeds in as little as five minutes; thus, the stannylated 3-quinuclidinyl benzilates may be converted to *AQNB in situ for immediate use. Using this method, radiolabelling yields as high as 80% have been observed. The present invention also is directed towards a method of synthesis of the stannylated 3-quinuclidinyl benzilate compounds. The method comprises providing a 4'-halo-3-quinuclidinyl benzilate and reacting the 4'-halo-3-quinuclidinyl benzilate with a compound having the formula $(SnR_3)_2$, wherein R is an alkyl.

35 Claims, No Drawings

STANNYLATED 3-QUINUCLIDINYL BENZILATES AND METHODS OF PREPARING RADIOHALOGENATED DERIVATIVES

TECHNICAL FIELD OF THE INVENTION

The present invention is directed towards the preparation of the tomographic imaging agents *AQNB from stannylated 3-quinuclidinyl benzilate precursor compounds, wherein *A is a radioactive halogen. The stannylated 3-quinuclidinyl benzilate precursors and associated methods of production of these compounds also fall within the purview of the present invention.

BACKGROUND OF THE INVENTION

In the peripheral nervous system, all internal organs innervated by the parasympathetic nervous system have muscarinic cholinergic receptors (mAChrs). For example, the heart, gastrointestinal tract, urinary bladder, sweat glands, lacrimal glands, blood vessels, and pupils are all innervated through muscarinic receptors. The central nervous system is also comprised of a complex network of muscarinic receptors, both pre- and postsynaptic. In particular, neurotransmission of acetylcholine is effected by means of muscarinic cholinergic receptors. Muscarinic cholinergic receptors in the brain mediate some of the effects of acetylcholine and cholinergic drugs, and are implicated in many CNS diseases.

Muscarinic cholinergic receptors constitute a family of related proteins. At present, five different mACHr proteins have been cloned and sequenced from the human and rat geonomes; three are known to correspond to pharmacologically defined proteins. See Palacios, J. M. et al., "Cholinergic Receptors in the Rat and Human Brain," *Progress in Brain Research* 84: 243 (1990). These receptors play a vital role in a number of psychological and behavioral responses, such as the mediation of sleep, avoidance behavior, learning, and memory. Eckelman, W. C. et al., "External Imaging of Cerebral Muscarinic Acetylcholine Receptors," *Science* 223: 291 (1984); Holman, B. L. et al., "Muscarinic Acetylcholine Receptors in Alzheimer's Disease," *JAMA* 254: 3063 (1985). In addition, many diseases are manifested through elevated or reduced mAChr levels in the brain, for example, Alzheimer's disease and other illnesses characterized by primary degenerative dementia. See, e.g., Weinberger, D. R. et al., "A Comparison of FDG PET and IQNB SPECT in Normal subjects and Patients with Dementia," *J. Neuropsychiatry & Clin. Neurosciences* 4: 239 (1992); Weinberger, D. R. et al., "The Distribution of Cerebral Muscarinic Receptors In Vivo in Patients with Dementia," *Arch Neurol.* 48: 239–248 (1992); Holman, B. L. et al., "Muscarinic Acetylcholine Receptors in Alzheimer's Disease," *JAMA* 254: 3063 (1985).

Tomographic imaging has emerged as a leading diagnostic tool for diagnosing and researching mAChr activity. In particular, single-photon emission-computed tomography (SPECT) has been used with much success in this area. In SPECT, a radioactive imaging agent is introduced into the subject, where it binds to a receptor in the cells of the subject. Typically, the subject's brain is then scanned with a SPECT scanner, such as the GERASPECT, Digital Scintigraphics, Inc., Waltham, Mass., and the presence of the radioactive imaging agent is detected and observed through the resulting images. See Owens J., et al. "Synthesis of (R,R) [123]IQNB," *J. Labelled Compounds and Radiopharmaceuticals* 31: 45 (1991); Weinberger, D. R. et al., "Neuropsychopharmacological Imaging with SPECT," *Clin. Neuropharm* (Suppl. 1): 194A (1992); see generally Neumeyer, J. L. et al., "$^{123}$I-2β-Carbomethoxy-3β-(4-iodophenyl) Tropane," *J. Med. Chem.* 34:3144 (1991).

Where mAChr is the receptor to be examined, the imaging agent typically employed is *IQNB. This diastereomeric compound is a strong muscarinic cholinergenic receptor antagonist having the following formula:

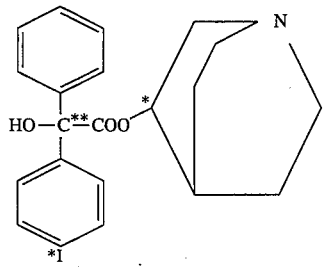

wherein C* and C** are chiral atoms, and *I is a radioactive isotope of iodine, such as $^{123}$I. The four isotopes of *IQNB, namely, (R,R), (R,S), (S,R), and (S,S), are all useful in tomographic imaging studies. By convention, (R,S) refers to the configuration wherein C* has a chirality of R and C** has a chirality of S. See Gibson, R. E. et al., "In Vitro and In Vivo Characteristics of [Iodine-125]-3(R)-Quinuclidinyl-(S)- 4 iodobenzilate" *J. Nucl. Med.* 30: 1079 (1989). Similarly, (S,R) refers to the configuration in which C* has a chirality of S and C** has a chirality of R.

It has been observed that the (R,R) diastereomer of *IQNB has high selectivity when binding to muscarinic cholinergic receptor sites, whereas the (S,S) diastereomer has low binding selectivity. See generally Gibson, R. E. et al., "In Vitro and In Vivo Characteristics of [Iodine-125]-3(R)-Quinuclidinyl-(S)-4-iodobenzilate" *J. Nucl. Med.* 30: 1079 (1989); Gibson, R. E. et al., "The Characteristics of I-125 4-IQNB and H-3 QNB In Vivo and In Vitro," *J. Nucl. Med.* 24: 214–222 (1984); Eckelman, W. C. et al., "Use of 3-Quinuclidinyl 4-Iodobenzilate as a Receptor Binding Radiotracer," *J. Nucl. Med.* 26: 637 (1985). Thus, the (S,S) diastereomer may be used as a reference compound for interpreting the tomographic images. Sawanda, Y. et al., "Kinetic Analysis of 3-Quinuclidinyl-4-[$^{125}$I] Iodobenzilate Transport and Specific Binding to Muscarinic Acetylcholine Receptor in Rat Brain In Vivo," *Cereb. Blood Flow Metab.* 10: 781 (1990). Other radioactive halogens may be used in place of iodine, for example, $^{78}$Br. When a radioisotope of iodine is used, the isotope preferably is $^{123}$I.

At present, the potential of SPECT imaging of muscarinic receptors as a diagnostic and analytical tool has not been fully attained, primarily due to the high cost and difficulty of synthesizing *IQNB. The radioisotopes of iodine have short half-lives, and thus any reactions involving these isotopes ideally should proceed as quickly as possible to avoid radiodecay of the iodine. For example, $^{123}$I has a half-life of only thirteen hours. Ideally, a synthesis of *IQNB should take only a few minutes to complete, thus allowing for in situ synthesis of *IQNB, and should result in a high radiolabelling yield. Preferably, the synthesis should afford a yield of at least 75%.

Although a number of methods of synthesizing *IQNB are known, no method is known that is capable of preparing *IQNB in such a short time with such high radiolabelling yields. For example, with respect to the conventional Wallach triazine approach, this method requires a reaction time of more than one hour at 80° C., and results in a product with a radiolabelling yield only up to about 20%. Rzeszotarski, W. J. et al., "Synthesis and Evaluation of Radioiodinated Derivatives of 1-Azabicyclo [2.2.2] oct-3-yl-α-4-iodophyenyl-α-phenylacetate as Potential Radiopharmaceuticals," *J. Med Chem.* 27: 156 (1984); Cohen, V. I. et al., "Preparation and Properties of (R)-(–)-1-Azabicyclo [2.2.2]-(R)(+)-α-hydroxy-α-4[$^{125}$I] iodophenyl-2-phenyl Acetate and R-(–)-1-Azabicyclo [2.2.2] oct. 3-yl-(S)-α-hydroxy-α-(4-[$^{125}$I] iodophenyl)-α-phenyl Acetate as Potential Radiopharmaceuticals, *J. Pharmaceutical Sciences* 78: 833 (1989). Radioiodination of QNB in trifluoroacetic acid has also been reported; however, this process results in a radiolabelling yield of only up to about 10% after 24 hours reaction time. Lee K. S. et al., "Radioiodination of 3-Quinuclidinyl Benzilate Using No-Carrier-Added Concentration of I-125-NaI," *J Nucl. Med.* 27: 1045 (1986). Yields of up to about 30% have been reported via a copper-assisted nucleophilic exchange method. Owens J., et al. "Synthesis of (R,R) $^{123}$IQNB," *J. Labelled Compounds and Radiopharmaceuticals* 31: 45 (1991). Recently, yields of up to 60% of $^{125}$IQNB have been reported via a QNB-boronic acid approach. Kabalka, G. W. et al., "Synthesis of Iodine- 125-Labeled-3-Quinuclidinyl 4'-Iodobenzilate," *Nucl. Med. Biol.* 16: 359 (1989). This method, however, requires a reaction time of one hour, and still fails to attain satisfactory yields.

As a result of the shortcomings of known methods of *IQNB preparation, the cost of *IQNB has made SPECT imaging prohibitive for many laboratories and hospitals. Thus, a clear need exists for a new method of synthesizing *IQNB that overcomes these drawbacks, particularly, the long reaction times and low radiolabelling yields associated with known methods. The present invention seeks to provide such a method, as well as compounds useful in such a method.

BRIEF SUMMARY OF THE INVENTION

The present invention provides stannylated 3-quinuclidinyl benzilate compounds and, further, a method of synthesizing *AQNB by halogenating, particularly iodinating such stannylated 3-quinuclidinyl benzilate compounds. The halogenation of these stannylated 3-quinuclidinyl benzilates proceeds in as little as five minutes; thus, the stannylated 3-quinuclidinyl benzilates may be converted to *AQNB in situ for immediate use. Using this method, radiolabelling yields as high as 80% have been observed when making *IQNB.

The present invention also provides a method of synthesis of the stannylated 3-quinuclidinyl benzilate compounds. The method comprises providing a 4'-halo-3-quinuclidinyl benzilate and reacting the 4'-halo-3-quinuclidinyl benzilate with a compound having the formula $(SnR_3)_2$, wherein R is an alkyl.

DESCRIPTION OF THE PREFERRED EMBODIMENTS

The present invention provides stannylated 3-quinuclidinyl benzilates having the formula

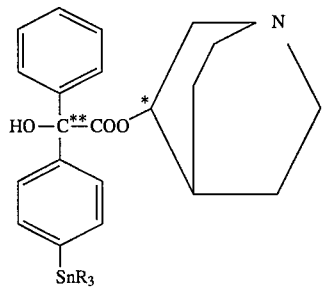

wherein R is selected from the group consisting of methyl, ethyl, propyl, butyl, and pentyl, including straight or branched $C_3$–$C_5$ radicals in the case where R is propyl, butyl, or pentyl. The designation "$SnR_3$" is intended to encompass the radical "$SnR^1R^2R^3$," wherein $R^1$, $R^2$, and $R^3$ are the same or different, and wherein each of $R^1$, $R^2$, and $R^3$ is defined as above. The substituents $R^1$, $R^2$, and $R^3$ are preferably the same and are preferably butyl.

In the compounds of the present invention, both C* and C** are chiral atoms. The chirality of C* is independent of the chirality of C**, and each atom may have either the R or S configuration. Because C* and C** are chiral atoms, four possible diastereomers exist, namely, the (R,R), (R,S), (S,R), and (S,S) diastereomers. Each diastereomer is useful in preparing the corresponding *AQNB diastereomer, thus, all of these configurations fall within the scope of the present invention.

Either phenyl ring may be substituted with one or more substituents, such as methyl. In addition, the quinuclidinyl ring may be substituted in one or more places, thus possibly creating one or more additional chiral centers. Any substituent may be placed onto either of the phenyl rings or onto the quinuclidinyl ring, so long as the ability to bind to muscarinic cholinergic receptors remains satisfactory for imaging and, in the case of in vivo imaging, so long as the toxicity of the substituted *AQNB remains tolerable.

The stannylated 3-quinuclidinyl benzilate compounds of the present invention may be synthesized from quinuclidinol and phenyl-(4-halophenyl) ketone according to the following general synthesis scheme. R-quinuclidinol and/or S-quinuclidinol are prepared from a racemic mixture of RS-quinuclidinol. Also prepared is a racemic mixture of RS-α-hydroxy-α-(4-halophenyl) phenylacetic acid, which preferably is then resolved into its R- and S-stereoisomers. These steps need not be performed in any particular order. Next, the desired diastereomer of 4'-halo- 3-quinuclidinyl benzilate is prepared. This compound has the formula

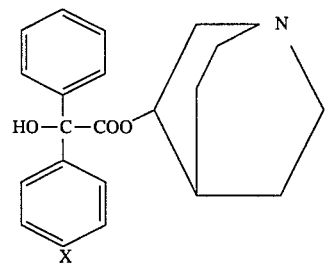

wherein X is selected from the group consisting of bromo and iodo, and is preferably bromo. Finally, this 4'-halo- 3-quinuclidinyl benzilate is converted to the corresponding stannylated 3-quinuclidinyl benzilate. The preferred reactions for accomplishing these syntheses are set forth below, although the present invention is not limited to these particular reactions.

PREPARATION OF R-QUINUCLIDINOL AND S-QUINUCLIDINOL FROM A RACEMIC MIXTURE OF RS-QUINUCLIDINOL

Using this synthesis, either R- or S-quinuclidinol may be independently prepared.

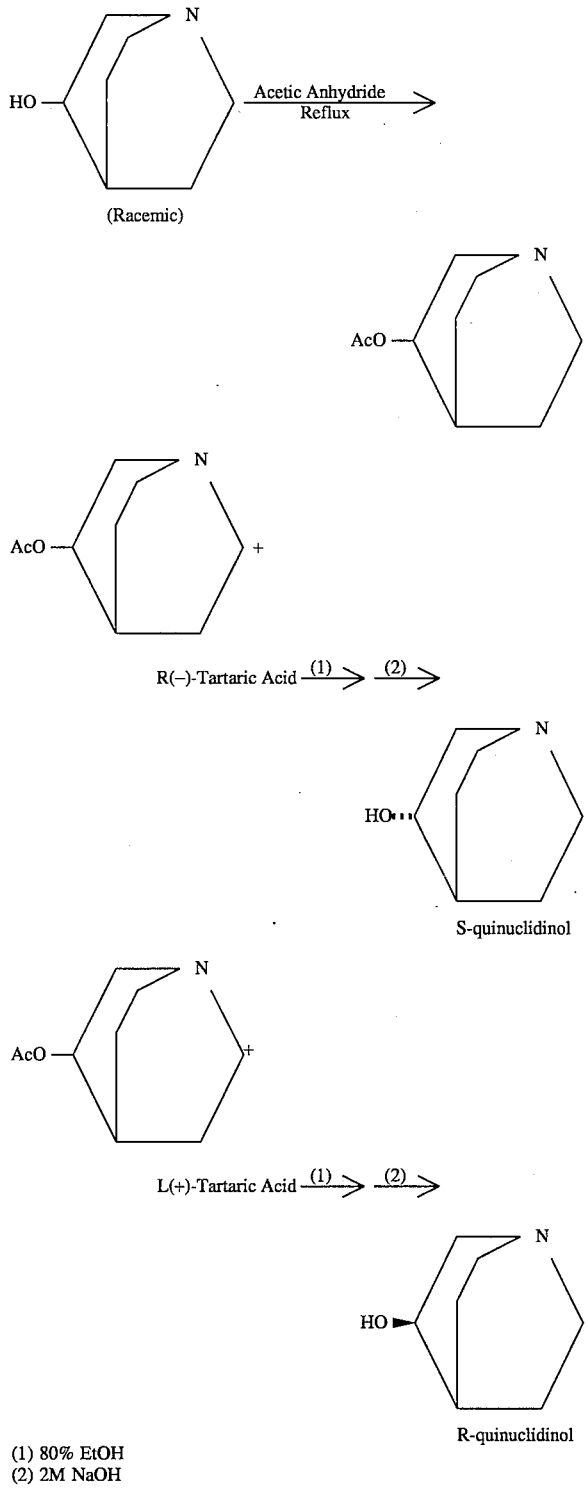

(1) 80% EtOH
(2) 2M NaOH

PREPARATION OF R-α-HYDROXY-α-(4-HALOPHENYL) PHENYLACETIC ACID AND S-α-HYDROXY-α-(4-HALOPHENYL) PHENYLACETIC ACID FROM PHENYL(4-HALOPHENYL) KETONE

Using this synthesis, a racemic mixture of RS-α-hydroxy-α-(4-halophenyl) phenylacetic acid is prepared.

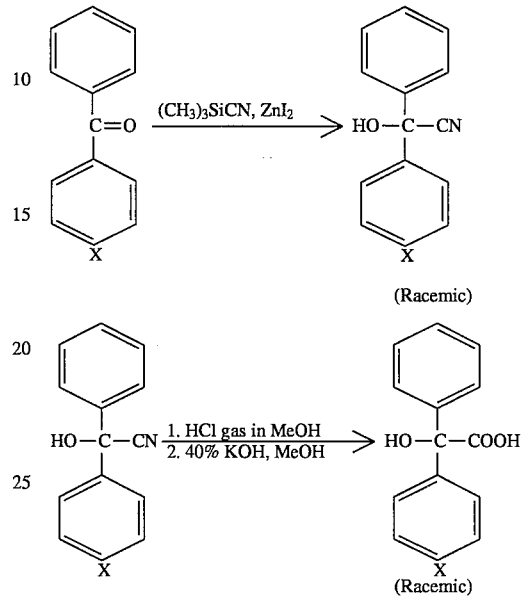

RESOLUTION OF RS-α-HYDROXY-α-(4-HALOPHENYL) PHENYLACETIC ACID

The racemic mixture of RS-α-hydroxy-α-(4-halophenyl) phenylacetic acid can be resolved into R- and S-components, although the racemic mixture need not be resolved prior to reaction with quinuclidinol. If the mixture is not resolved at this stage, then addition of the R- or S-quinuclidinyl will result in a mixture of (R,RS) 4'-halo-3-quinuclidinyl benzilate, having an unresolved C atom. The C center may be resolved at this stage, or, alternatively, the resolution of the stereoisomers may occur at a later point in the synthesis, even after *AQNB has been prepared. Preferably, however, the C** chiral center is resolved at the RS-α-hydroxy-α-(4-halophenyl) phenylacetic acid intermediate.

Resolution of the stereoisomers is accomplished using a solution of quinine or quinidine in EtOAc. The S(+)-isomer crystallizes as its quinidine salt in a solution of quinidine and EtOAc, and the R(−)-isomer crystallizes as its quinine salt in a solution of EtOAc and MeOH. Each isomer may then be readily isolated with acid for further reaction.

PREPARATION OF 4'-HALO-3-QUINUCLIDINYL BENZILATE

Any diastereomer of 4'-halo-3-quinuclidinyl benzilate may be prepared according to the reactions set forth below. Preferably, the reactions take place in the presence of carbonyldiimidazole and DMF.

R-α-hydroxy-α-(4-halophenyl) phenylacetic acid+R-quinuclidinol→(R,R) 4'-halo-3-quinuclidinyl benzilate;
S-α-hydroxy-α-(4-halophenyl) phenylacetic acid+R-quinuclidinol→(R,S) 4'-halo-3-quinuclidinyl benzilate;
R-α-hydroxy-α-(4-halophenyl) phenylacetic acid+S-quinuclidinol→(S,R) 4'-halo-3-quinuclidinyl benzilate;
S-α-hydroxy-α-(4-halophenyl) phenylacetic acid+S-quinuclidinol→(S,S) 4'-halo-3-quinuclidinyl benzilate.

PREPARATION OF STANNYLATED 3-QUINUCLIDINYL BENZILATES

Any diastereomer of the stannylated 3-quinuclidinyl benzilates of the present invention may be prepared by stannylating the corresponding 4'-halo-3-quinuclidinyl benzilate. Preferably, the stannylation is accomplished by reacting the 4'-halo-3-quinuclidinyl benzilate with a compound having the formula $(SnR_3)_2$, as previously described. This reaction preferably occurs in triethylamine solution in the presence of the catalyst $Pd[P(C_6H_5)_3]_4$. For example, if (R,S) stannylated 3-quinuclidinyl benzilate is desired, this compound can readily be prepared by reacting (R,S) 4'-halo-3-quinuclidinyl benzilate with $(SnR_3)_2$ in triethylamine solution in the presence of $Pd[P(C_6H_5)_3]_4$.

The present invention also encompasses a method of preparing *AQNB, wherein *A is a radioactive halogen. Preferably, *A is an isotope of iodine, most preferably $^{123}I$. To prepare *AQNB, the stannylated 3-quinuclidinyl benzilate is halogenated. Preferably, the stannylated 3-quinuclidinyl benzilate is halogenated by reaction with Na*A in the presence of a reagent that is capable of oxidizing the *A$^-$, such as 0.32% peracetic acid. The reaction is then quenched, preferably with a reducing agent such as $NaHSO_3$. The *AQNB thus formed may be rapidly isolated via reverse-phase HPLC or short column chromatography using ethanol or ethyl acetate, or may be administered directly to the cell to be imaged without isolating the *AQNB from solution. Preferably, the *AQNB is dissolved in ethanol and saline solution before administration in vivo.

One skilled in the art will immediately appreciate that this reaction may be performed in situ immediately prior to administration to the cell to be imaged. The stannylated 3-quinuclidinyl benzilate may be prepared well in advance, and quickly and easily halogenated in a simple reaction, and, if desired, rapidly isolated. Another significant advantage of the present inventive synthesis is that it affords extremely high radiolabelling yields of *AQNB. Radiolabelling yields of as high as 80% have been observed using the compounds and methods of the present invention. It is believed that such high yields are observed because the halogenation occurs in a single step, thus minimizing side reactions.

The following examples further illustrate the present invention but, of course, should not be construed as in any way limiting its scope.

EXAMPLE 1

This example provides an illustration of a stannylated 3-quinuclidinyl benzilate compound according to the present invention and of a method of preparing the compound.

A stannylated 3-quinuclidinyl benzilate compound having the following formula was prepared.

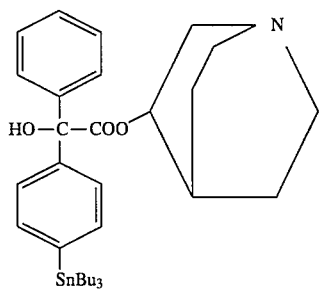

The compound was prepared as follows.
A. Preparation of R- and S-isomers of 3-quinuclidinol A racemic mixture of (RS) 3-quinuclidinol was dissolved in acetic anhydride and refluxed for three hours to yield a racemic mixture of (RS) 3-acetoxy quinuclidine (b.p. 61°–63° C./0.26 mm Hg; 95% yield). To a boiling solution of 28.28 g of this racemic mixture was added a boiling solution of 25.1 g L-(+)-tartaric acid dissolved in 60 ml of 80% ethanol. The solution was allowed to cool to room temperature, then allowed to stand for several hours, yielding crystals of the (+) hydrogen tartrate salt of 3-acetoxy quinuclidine. This salt was recrystallized three times in 80% ethanol to give 16.77 g of colorless crystals (m.p. 93°–96° C. (froths)). In like manner, the free base obtained from the first mother liquor was then treated with R(–)-tartaric acid and recrystallized to yield 14.5 g of colorless crystals of the (–) hydrogen tartrate salt (m.p. 93°–97° C. (froths)).

The R-isomer of 3-quinuclidinol was prepared by dissolving 15 g of the (+) hydrogen tartrate salt in 150 ml 2M NaOH and saturating the solution with $K_2CO_3$. The solution was heated for 50 min at 60° C., then extracted with $CHCl_3$. The extracts were dried over anhydrous $Na_2SO_4$ and evaporated in vacuo to yield a white solid. The solid was recrystallized in acetone to yield 5.11 g colorless crystals (m.p. 220°–221° C.; $[\alpha]_D$ –44.41° (C 3.22, 1N HCl)). In like manner 4 g of S-3-quinuclidinol (m.p. 220.5°–221° C.; $[\alpha]_D$+44.18° (C 3.22, 1N HCl)) were prepared from 12.5 g (–) hydrogen tartrate salt.

B. Preparation of R- and S-isomers of α-hydroxy-α-(4-bromophenyl) phenylacetic acid To a stirred solution of 55 g 4-bromobenzophenone in 450 ml amylenes-stabilized $CHCl_3$ was added 25 g of trimethylsilyl cyanide, followed by 3 g of fresh baked zinc iodide. The mixture was stirred at room temperature under a nitrogen blanket for 65 hours, refluxed for 50 hours, then evaporated in vacuo to yield a brown oil. The oil was suspended in 400 ml 3N HCl and stirred at room temperature for several hours. Some semi-solid material was formed and extracted with EtOAc. The combined extracts were washed with saturated saline solution to pH 7, dried over anhydrous $Na_2SO_4$, and evaporated in vacuo to yield a pale yellow solid. The solid was recrystallized in a mixture of EtOAc and hexanes to give 45.14 g colorless crystals (m.p.=110°–111° C.).

The crystals (14.4 g; 0.05 mol) were dissolved in 300 ml methanol and stirred in an ice bath. The solution was saturated with HCl gas and stirred at room temperature overnight, then evaporated in vacuo to yield a white foam. To the foam was added 100 ml methanol and 200 ml 40% KOH. The mixture was stirred and refluxed under a nitrogen blanket for several hours. After cooling, the mixture was diluted with water and extracted with diethyl ether. The solution was acidified with concentrated HCl to pH 2 and extracted with $CHCl_3$. The extract was dried and evaporated in vacuo to yield a yellow oil, which yielded 10.06 g colorless crystals in aqueous methanol (m.p. 126°–127.5° C.).

In boiling EtOAc (20 ml), 3.07 g of the (RS)-α-hydroxy-α-(4-bromophenyl) phenylacetic acid thus formed was added to 3.24 g quinidine (Aldrich, 97%) dissolved in boiling EtOAc (40 ml). The mixture was allowed to cool to room temperature and stand for several hours. The salt which crystallized was filtered off and recrystallized five times from EtOAc to yield 1.39 g colorless crystals (m.p. 116°–117° C.; $[\alpha]_D$+141° (C 0.49, MeOH)). Of these crystals, 0.96 g were suspended in 5N HCl, stirred at room temperature for 40 minutes, then extracted with $CH_2Cl_2$. The extracts were washed with 3N HCl and $H_2O$, dried, and evaporated in vacuo to yield a white solid. The solid was recrystallized in aqueous methanol to yield 367.7 mg colorless crystals of S(+)-α-hydroxy-α-(4-bromophenyl) phenylacetic acid (m.p. 136°–137° C., $[\alpha]_D$+24.35° (0.78, $CHCl_3$))).

To obtain the R(–)-isomer, the first mother liquor was evaporated to yield a yellow oil. The oil was suspended in 6N HCl for 1 hour, and then was extracted with $CH_2Cl_2$. The $CH_2Cl_2$ extracts were washed with 20% HCl and $H_2O$, dried, and evaporated to yield a pale yellow solid. The solid was treated with quinine (Aldrich, 90%) in boiling EtOAc and methanol (10:1) to give colorless crystals. The crystals were recrystallized six times until the melting point remained constant (194.5°–195° C.; $[\alpha]_D$–115.28° (C 0.39, MeOH)). One gram of the crystals was suspended in 5N HCl, stirred at room temperature for 40 minutes, and then was extracted with $CH_2Cl_2$. The extracts were washed with 3N HCl and $H_2O$, dried, and evaporated in vacuo to yield a white solid. The solid was recrystallized in aqueous methanol to yield 367.7 mg colorless crystals of R(–)-α-hydroxy-α-(4-bromophenyl) phenylacetic acid (m.p. 136°–137° C.; $[\alpha]_D$–26° (C 0.72, $CHCl_3$)).

C. Preparation of 4'-bromo-3-quinuclidinyl benzilate

To a solution of 921 mg of (RS)-α-hydroxy-α-(4-halophenyl) phenylacetic acid in 10 ml DMF was added a solution of 486 mg N,N'-carbonyldiimidazole in 10 ml DMF. The solution was stirred at room temperature for 1 hour under a nitrogen blanket. To the solution was added a solution of 381 mg racemic quinuclidinol in 15 ml DMF. The mixture was stirred for several hours, then poured into a mixture of water and diethyl ether. The separated aqueous layer was extracted with ether, and the combined ether phases were washed with water, dried, and evaporated in vacuo to yield a white foam. The foam was crystallized in acetonitrile to yield 0.79 g colorless crystals of (RS,RS) 4'-bromo-3-quinuclidinyl benzilate. In like manner, the four diastereomers of 4'-bromo-3-quinuclidinyl benzilate were separately prepared.

D. Preparation of 3'quinuclidinyl-(4'-tributyltin) benzilate

To a solution of 415 mg (RS,RS) 4'-bromo-3-quinuclidinyl benzilate in triethylamine (15 ml) was added 116 mg $Pd[P(C_6H_5)_3]_4$ and 700 mg $(SnBu_3)_2$. The mixture was refluxed under a nitrogen blanket for several hours, then cooled and filtered. The filtrate was evaporated in vacuo to yield a black oil, which was passed through a silica gel column and eluted with $CH_2Cl_2$ and $CH_2Cl_2$/MeOH (100:1 and 100:3). The fractions were combined and evacuated to yield 229 mg of a colorless oil.

EXAMPLES 2–5

These examples provide a further illustration of stannylated 3-quinuclidinyl benzilate compounds according to the present invention, and of a method for preparing these compounds.

Stannylated 3-quinuclidinyl benzilate compounds having the following formulae can be prepared.

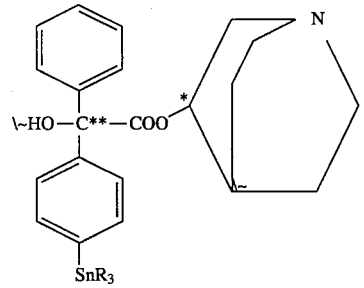

| Example | R |
|---------|---|
| 2 | —$CH_3$ |
| 3 | —$CH_2CH_3$ |
| 4 | —$CH_2CH_2CH_3$ |
| 5 | —$CH_2CH_2CH_2CH_2CH_3$ |

These compounds can be prepared in accordance with the method set forth in Example 1, except that $(SnR_3)_2$ is used in place of $(SnBu_3)_2$.

EXAMPLE 6

This example illustrates the preparation of $^{123}$IQNB and $^{125}$IQNB according to the present invention.

The compound prepared in accordance with Example 1 was reacted with Na*A, wherein *A was $^{123}$I, so as to yield $^{123}$IQNB. Aqueous peracetic acid (100 ul, 0.32% w/v) was added to a reaction mixture containing 100 ul (1 mg/ml) of (RS,RS) 3'quinuclidinyl-(4'-tributyltin) benzilate, 200 ul ethanol, 40 ul 1N HCl, and no-carrier-added Na$^{123}$I. The reaction was allowed to stand for five minutes at room temperature, and was then quenched by adding 20 mg $NaHSO_3$. The reaction mixture was made basic by adding 25 mg $NaHCO_3$. The $^{123}$IQNB thus formed was added to a 1 ml octadecyl reverse-phase HPLC column and eluted with ethanol. The product was concentrated to 200 ul in a nitrogen stream, and 1–2 ml 0.9% saline was added. The solution was then filtered through a sterile 0.22 micron Millipore filter. The overall radiochemical yield was 80%.

An alternate purification method was also employed. The reaction mixture resulting from the formation of $^{123}$IQNB was extracted with three 1 ml aliquots of ethyl acetate. The combined organic extracts were washed with 1 ml of water, and the organic layer was evaporated to dryness in a stream of nitrogen. Ethanol was added to the product, followed by 1–2 ml 0.9% saline solution. The solution was then filtered through a sterile 0.22 micron Millipore filter. In some cases, the dried organic extracts were mixed with 100 ul ethanol and purified by reverse-phase HPLC on an octadecyl column (PRP-1, 250×4.1 mm, Hamilton Co.) using a 60% solution by weight of methanol in water. The product fraction was collected and extracted with three 1 ml aliquots of ethyl acetate. The combined organic extracts were evaporated to dryness in a stream of nitrogen. Ethanol was added to the product, followed by 1–2 ml 0.9% saline solution. The solution was then filtered through a sterile 0.22 micron Millipore filter.

Similarly, the compound prepared in accordance with Example 1 was reacted with Na$^{125}$I to form $^{125}$IQNB.

The nonradioactive compound $^{127}$IQNB was also prepared in racemic mixture by adding a solution of 0.1 mol iodine in $CHCl_3$ to a racemic mixture of 45 mg 3'quinuclidinyl-(4'-tributyltin) benzilate. The iodine was added dropwise until the iodine color persisted, and the mixture was stirred overnight. To the mixture was added 1 ml KF in 1M methanol, then 2 ml of 5% $Na_2S_2O_5$. The mixture was extracted with $CHCl_3$, and the extracts were dried and evaporated in vacuo to yield a pale yellow semi-solid. The solid was treated to preparative TLC (silica gel, $CH_2Cl_2$, $CH_3OH$, $NH_4OH$) to give 27 mg of (RS,RS) $^{127}$IQNB.

EXAMPLES 7–10

These examples further illustrate the preparation of $^{123}$IQNB and $^{125}$IQNB according to the present invention.

In a manner similar to that of Example 6, the compounds of Examples 2–5 can be reacted with Na*A, wherein *A is $^{123}$I, so as to yield $^{123}$IQNB. Similarly, the compounds of Examples 2–5 can be reacted with Na*A, wherein *A is $^{125}$I, so as to yield $^{125}$IQNB.

While particular embodiments of the invention have been shown, it will of course be understood that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention. All references previously cited are herein incorporated by reference in their entireties.

What is claimed is:

1. A compound of the formula

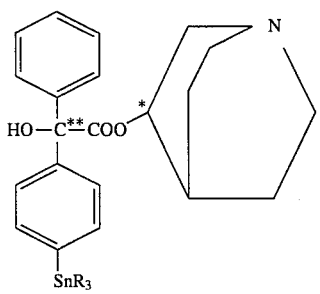

wherein R is selected from the group consisting of methyl, ethyl, propyl, butyl, and pentyl.

2. A compound according to claim 1, wherein R is butyl.

3. A compound according to claim 2, wherein C* has the chiral form R.

4. A compound according to claim 3, wherein C** has the chiral form R.

5. A compound according to claim 3, wherein C** has the chiral form S.

6. A method of preparing a compound having the formula

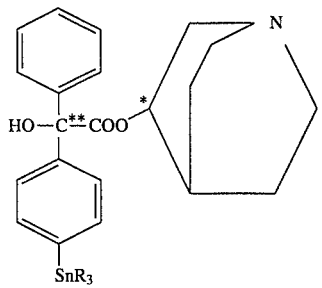

wherein R is selected from the group consisting of methyl, ethyl, propyl, butyl, and pentyl, said method comprising providing a 4'-halo-3-quinuclidinyl benzilate of the formula

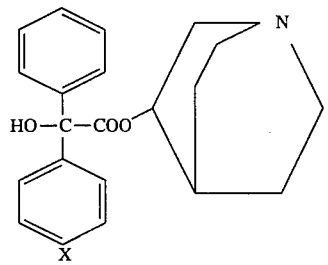

wherein R is selected from the group consisting of methyl, ethyl, propyl, butyl, and pentyl and X is selected from the group consisting of bromo and iodo, and reacting said 4'-halo- 3-quinuclidinyl benzilate with a compound having the formula (SnR$_3$)$_2$.

7. A method according to claim 6, wherein X is iodo.

8. A method according to claim 6, wherein X is bromo.

9. A method according to claim 8, wherein R is butyl.

10. A method according to claim 9, wherein said 4'-halo-3-quinuclidinyl benzilate has the chiral form (R,R).

11. A method according to claim 9, wherein said 4'-halo-3-quinuclidinyl benzilate has the chiral form (R,S).

12. A method according to claim 9, wherein said 4'-halo-3-quinuclidinyl benzilate is prepared by reacting a quinuclidinol having the formula

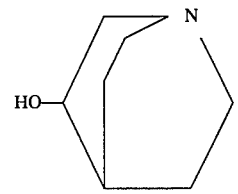

with an α-hydroxy-α-(4-halophenyl) phenylacetic acid having the formula

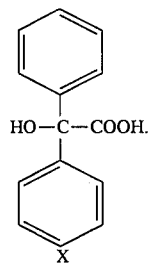

13. A method according to claim 12, wherein said quinuclidinol has the chiral form R.

14. A method according to claim 13, wherein said α-hydroxy-α-(4-halophenyl) phenylacetic acid has been resolved prior to reacting with said quinuclidinol.

15. A method according to claim 14, wherein said α-hydroxy-α-(4-halophenyl) phenylacetic acid has the chiral form R.

16. A method according to claim 14, wherein said α-hydroxy-α-(4-halophenyl) phenylacetic acid has the chiral form S.

17. A method of preparing *AQNB, wherein *A is selected from the group consisting of the radioactive halogen isotopes, said method comprising providing a stannylated 3-quinuclidinyl benzilate having the formula

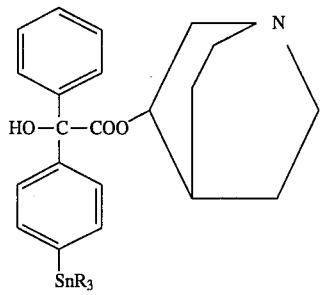

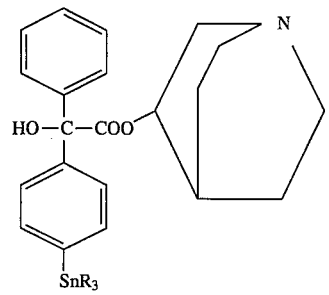

wherein R is selected from the group consisting of methyl, ethyl, propyl, butyl, and pentyl, and halogenating said stannylated 3-quinuclidinyl benzilate to form said *AQNB.

18. A method according to claim 17, wherein *A is iodine.

19. A method according to claim 18, wherein *A is selected from the group consisting of $^{123}$I, $^{125}$I, $^{127}$I, and $^{131}$I.

20. A method according to claim 19, wherein R is butyl.

21. A method according to claim 20, wherein *A is $^{123}$I.

22. A method according to claim 20, wherein *A is $^{125}$I.

23. A method according to claim 20, wherein *A is $^{127}$I.

24. A method according to claim 20, wherein said *AQNB has the chiral form (R,R).

25. A method according to claim 20, wherein said *AQNB has the chiral form (R,S).

26. A method according to claim 20, wherein said halogenation is accomplished by reacting said stannylated 3-quinuclidinyl benzilate with Na*I.

27. A method according to claim 26, wherein said halogenation is accomplished by reacting said stannylated 3-quinuclidinyl benzilate with Na$^{123}$I.

28. A method of preparing *IQNB, wherein *I is selected from the group consisting of $^{123}$I, $^{125}$I, $^{127}$I, and $^{131}$I, said method comprising (a) providing a 4'-halo-3-quinuclidinyl benzilate of the formula

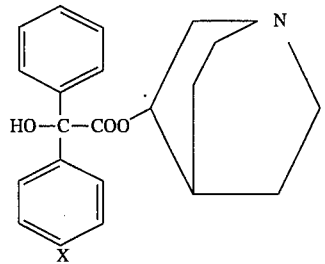

wherein X is selected from the group consisting of bromo and iodo;

(b) reacting said 4'-halo-3-quinuclidinyl benzilate with a compound having the formula (SnBu$_3$)$_2$ to form a stannylated 3-quinuclidinyl benzilate having the formula wherein R is butyl; and (c) halogenating said stannylated 3-quinuclidinyl benzilate to form said *IQNB.

29. A method according to claim 28, wherein said 4'-halo-3-quinuclidinyl benzilate has the chiral form (R,R).

30. A method according to claim 28, wherein said 4'-halo-3-quinuclidinyl benzilate has the chiral form (R,S).

31. A method according to claim 28, wherein said 4'-halo-3-quinuclidinyl benzilate is prepared by reacting a quinuclidinol having the formula

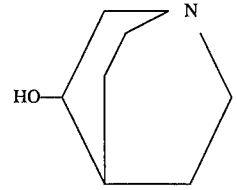

with an α-hydroxy-α-(4-halophenyl) phenylacetic acid having the formula

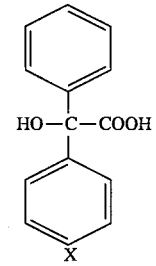

wherein X is selected from the group consisting of bromo and iodo.

32. A method according to claim 31, wherein said α-hydroxy-α-(4-halophenyl) phenylacetate has been resolved prior to reacting with said quinuclidinol.

33. A method according to claim 32, wherein said quinuclidinol has the chiral form R.

34. A method according to claim 33, wherein said α-hydroxy-α-(4-halophenyl) phenylacetic acid has the chiral form R.

35. A method according to claim 33, wherein said α-hydroxy-α-(4-halophenyl) phenylacetic acid has the chiral form S.

* * * * *